United States Patent [19]

Kulli

[11] Patent Number: 4,747,831
[45] Date of Patent: May 31, 1988

[54] CANNULA INSERTION SET WITH SAFETY RETRACTING NEEDLE

[75] Inventor: John C. Kulli, South Pasadena, Calif.

[73] Assignee: Phase Medical, Inc., Los Angeles, Calif.

[21] Appl. No.: 43,691

[22] Filed: Apr. 29, 1987

[51] Int. Cl.⁴ ............................................. A61M 5/24
[52] U.S. Cl. ................................. 604/110; 604/198
[58] Field of Search ............... 604/198, 197, 136, 138, 604/110, 162, 263, 194

[56] References Cited

U.S. PATENT DOCUMENTS

| | | | |
|---|---|---|---|
| 2,876,770 | 3/1959 | White | 604/198 |
| 3,314,428 | 4/1967 | Johnson et al. | 604/192 X |
| 3,890,971 | 6/1975 | Leeson et al. | 604/110 |
| 4,542,749 | 9/1985 | Caselgrandi | 128/752 |

*Primary Examiner*—Stephen C. Pellegrino
*Attorney, Agent, or Firm*—Ashen Golant Martin & Seldon

[57] ABSTRACT

A cannula insertion needle projects from the "forward" end of a hollow handle. After use to start a cannula, the needle is released from the end of the handle and its sharp end retracted into the handle, beyond reach. Preferably the handle has an aperture big enough for the needle but too small for fingertips. In one preferred form of the invention, the needle rides in a carrier block that slides inside the handle. Initially the block is secured in the handle against the forward end, with the sharp end of the needle protruding outward through the aperture. A manually releasable latch holds the block in this position. The latch mechanism includes mutually interfering stop elements on the exterior of the block and interior of the handle. After the cannula is in place, the person using the device withdraws the needle from the patient and manually triggers the carrier-block latch by squeezing or rotating one of the stop elements out of engagement with the other. Then a coiled spring drives the block rearward to retract the needle into the handle. At the rear end of the handle a stop halts the carrier block and needle so that they are safely confined within the handle. A standard-size tube fitting on the rear of the handle and a hollow needle permit liquid flow to or from the patient through the handle temporarily.

20 Claims, 5 Drawing Sheets

CANNULA INSERTION SET WITH SAFETY RETRACTING NEEDLE

BACKGROUND

1. Field of the Invention

This invention relates generally to medical appliances; and more particularly to a device for inserting a cannula—such as an intravenous cannula—into a patient's body.

2. Prior Art

As is well known, there are myriad very important medical uses for intravenous and intraarterial tubes and other indwelling catheters. It is also known in the medical community that a severe problem has developed in relation to all such devices.

That problem arises from the continuing presence of horrible diseases, particularly fatal and currently incurable diseases such as acquired immune deficiency syndrome ("AIDS") and hepatitis, transmitted by exchange of body substances between people. These diseases have led medical institutions to exclusively use disposable needles for injections and for catheter or cannula implants.

A severe residual risk remains, however, for medical personnel themselves in the inadvertent touching of needle tips after withdrawal from infected patients. Medical needles are designed and manufactured specifically to be extremely sharp and to puncture skin and flesh with only the slightest pressure.

As a result, what would ordinarily be an inconsequential scratch or pinprick can bring and has brought severe disease or even death to many medical staff members and others. Needless to say, health-care professionals are well aware of this risk and take considerable precautions to avoid such inadvertent punctures; thus the risk is reduced on a "probability" basis to an exceedingly small value.

Nevertheless, the exposure is so massive for working doctors, nurses and technicians that occasional punctures are inevitable. As a practical matter, it is virtually impossible for such an individual to reduce the incidence of accidental puncture to less than, say, one every year or perhaps one every few years.

Of course, not every such puncture follows contamination of the needle by a patient carrying a transmissible fatal disease. Nevertheless, there are enough medical personnel and enough such patients that a significant number of medical staffers die—and of course a greater number become very sick—from these accidents.

In discussion of this problem, needles of the types used with syringes commonly come to prominence. Though the word "hypodermic" has somewhat passed out of current usage in the medical profession, I shall for purposes of definiteness and simplicity refer to needles used with syringes for giving injections as "hypodermic needles." Needles used in drawing blood will be called "phlebotomy needles." By this terminology I mean to clearly distinguish all such needles from needles that are used for cannula insertion, the field of the present invention.

Hypodermic and phlebotomy needles are prominent in discussion because they are used so conspicuously and in such enormous quantity. Interestingly, however, the actual manual manipulations involved in using hypodermic and phlebotomy needles are relatively favorable to avoiding puncture accidents.

More specifically: after a hypodermic needle is withdrawn from a patient, the person using the needle in some circumstances (e.g., intramuscular injections) immediately has both hands available to properly deal with the needle. In normal circumstances he or she can promptly sheath and discard it before further tending to the patient.

In many other situations (e.g., intravenous injection) the person using the hypodermic needle almost always has one hand free to at least hold the needle until it can be properly sheathed. In some situations that are more demanding of dexterity (e.g., blood withdrawal), the person using the phlebotomy needle usually can at least find a second to place it temporarily well out of the way until there is time for safe disposal.

(It will be understood that my discussion here is directed to the relatively lower danger in procedures for injections or blood withdrawal, as contrasted with the procedures for cannula insertion. Thus I do not mean to imply that once properly sheathed, hypodermic needles used for intramuscular injections are necessarily safe: there of course remains a certain amount of potential for inadvertent unsheathing and many other kinds of accidents.)

Of course there are exceptions to the foregoing general proposition that injection and phlebotomy procedures are relatively less dangerous than cannula-insertion procedures. There are learning situations and emergencies, and circumstances in which the usual manipulations are complicated by patient mental or physical condition. These are, however, probably only between ten and twenty percent of all instances of use of hypodermic and phlebotomy needles.

Procedures for insertion of intravenous or other cannulae are not so favorable for avoidance of accidental punctures. When a cannula has been emplaced in a patient's blood vessel, for example, the cannula potentially forms an open channel for conveyance of the patient's blood to the outside of the body.

The patient's blood vessel must therefore be blocked firmly until and while this channel is connected to a mating tube—which is pressurized, typically with fluid to be infused into the patient's body. In practice the doctor, nurse or technician usually blocks the blood vessel by pressing manually on the outside of the patient's body, just at the tip of the cannula.

This pressure is maintained continuously until the tube is attached to the cannula. From this it will be understood that, before the medical staff member will have both hands free, there will be an intermediate time during which neither hand is free.

In some instances the needle used to emplace the cannula is hollow, and the tubing can be temporarily connected to the back of that needle. This is in fact only temporary relief, however, since eventually the tubing must be removed from the needle, the needle removed from the patient, and the tube reconnected to the cannula.

In some cases the person using the needle is able to place nearby, in advance, a tray in which to temporarily deposit the unsheathed needle without moving out of arm's reach of the patient. This option is not always available, however, and in any event using such a tray is itself a risky proposition.

As a result, a medical staff member who frequently start intravenous tubes and the like typically becomes adept at sheathing needles with one hand. Heretofore this has been the least problematical solution to a continuing problem.

It is nevertheless a very poor solution. It is precisely the kind of maneuver that sooner or later goes astray, leading to an occasional scratch or puncture and thereby statistically to severe illness or death.

Figure 16:
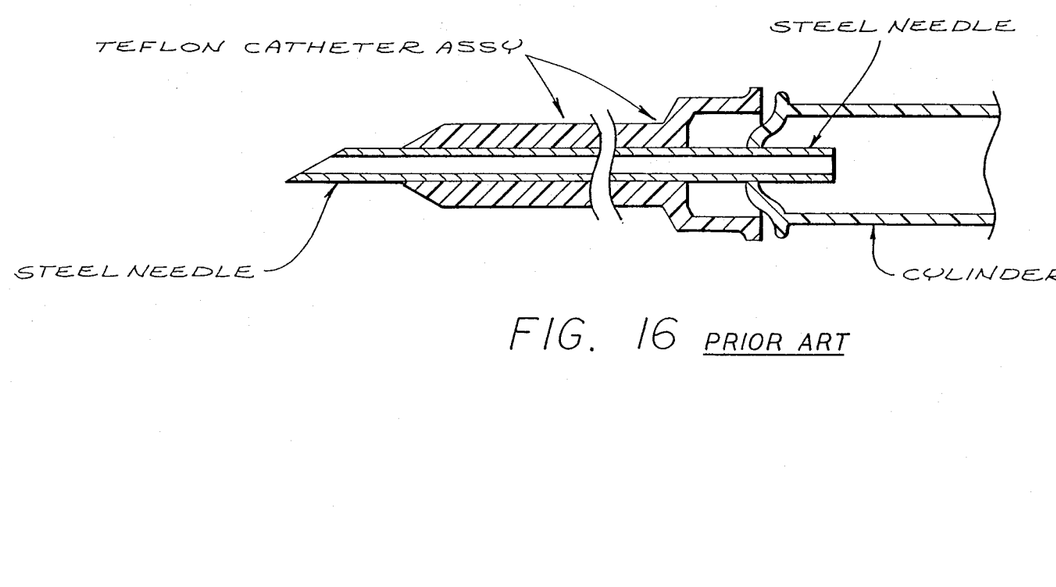
FIG. 16 is a somewhat schematic enlarged elevation, in longitudinal section, representative of the prior art.

FIG. 16 shows a device generally representative of present-day standard, commercially available cannula insertion kits. The familiar term in the health-care professions for such a prior-art device is "I. V. insertion set"—the initials standing for the word "intravenous."

The needle is stainless steel and extremely sharp at its frontal end, which is the left end as drawn in FIG. 16. The shank of the needle is permanently secured into the frontal end of a molded plastic cylinder, with the sharp end of the needle projecting forward out from the cylinder as illustrated. The cylinder may be typically made of polycarbonate.

For reasons that will shortly appear, the needle is preferably but not necessarily hollow. I am not familiar with the manufacturing details of these articles, but it would appear that the needle may be secured to the cylinder by a press fit or shrink fit, or by molding the plastic cylinder in place on the needle.

A separate catheter assembly or "cannula" fits very snugly, but removably, onto the forwardly projecting part of the needle. The tapered front of the cannula slides with the needle through a patient's skin and flesh.

The rear portion or hub of the cannula is radially enlarged and formed to define a very slightly tapered rearward receptacle for a standard-diameter tube, such as intravenous supply tubing. The cannula, or at least its part that is fitted snugly onto the shank of the needle, is of a biologically inert but very slippery material, such as that available commercially under the well-known trade name "Teflon." The hub is typically of high-molecular-weight polypropylene or the like.

In use the needle and cannula are inserted together into a patient's blood vessel—or in some cases into a body cavity, or an abscess, or wherever fluid communication is to be established. As previously mentioned, the medical staff person using the device then usually applies pressure to the outside of the patient's body just ahead of the needle tip, to prevent outward flow of blood.

The medical staff member then withdraws the needle, leaving the cannula in place within the body. Finally the fluid communication is completed by insertion of a standard-diameter tube into the receptacle at the rear end of the cannula.

In a typical cannula insertion set the rearward portion of the cylinder is formed very similarly to the rear end of the cannula, making allowance for the difference in properties of the cylinder and cannula materials. This shaping permits attachment of the standard tubing to the cylinder rather than the cannula.

In use, when it is not necessary or desirable to leave the cannula alone in the patient's body with the tubulation attached—or if it is not desirable to do so immediately—an intravenous or like connection can be made through the steel needle. It is for this reason that the needle is advantageously hollow.

A separate safety cover (not illustrated) is typically supplied in place on each insertion set. The separate safety cover firmly grips the cylinder and entirely covers the needle, to prevent accidental puncture and to prevent accidental contamination of the needle by substances in the environment, before use.

To use the insertion set, the safety cover must be entirely removed and set aside.

As already outlined, our focus of concern now shifts to the possibility that the needle may be contaminated by substances in the patient, during use. Accordingly the safety cover is to be replaced over the sharp end of the needle to prevent accidental puncture and, particularly, to prevent contact of people other than the patient, with possible contaminants on the needle.

It is here that the prior art fails to be effective, since the process of replacing the safety cover is subject to the risks previously described. As far as I know, the medical marketplace lacks any appliance or apparatus aimed at solving this problem.

The closest safety device that may be at all relevant is actually in a different field, namely the field of hypodermic needles. That device is a special form of hypodermic needle, available commercially from the firm ICU Medical, Inc. under the trade name "ICU High Risk Needle."

The ICU device is fitted with a sliding sheath that is carried on the shaft of the hypodermic needle itself. After use the sheath is advanced forward over the needle tip.

This device undoubtedly serves a useful purpose, and it is certainly not my desire to criticize what is apparently the only commercial effort directed to problems even remotely analogous to those of interest here. On the other hand, that device evidently has limitations that should be mentioned.

First, the ICU High Risk Needle is offered as a special item at a special price, for use only with patients known to be "high risk" patients. Not all patients carrying transmissible fatal diseases are known to be high risks.

Secondly, the sheath is attached halfway out the needle, where there would appear to be potential for inadvertent application of lateral force with sufficient leverage to snap off the needle. If that should occur before the sheath were fully advanced, the potential for accidental puncture could be substantial.

Thirdly, it is not clear from commercial literature on the product that the sheath locks in place when advanced—or, if so, that it locks firmly enough to withstand normal jarring in the workplace. Without such a feature, the device would seem to offer very limited protection.

Finally, as already suggested, the ICU product is neither designed nor offered for use in insertion of cannulae or the like. It appears to require substantial modification for any such use.

A number of patents have been issued for devices that shield medical needles, but they are virtually all for hypodermic or phlebotomy needles. Only one of these patents even mentions needles used in emplacing intravenous cannulae. That is U.S. Pat. No. 4,592,744, issued June 3, 1986, to Janine C. Jagger et al. The introductory passages of the Jagger patent refers to, e.g.

> safety venipuncture devices having needle retracting means, particularly hypodermic needles having a retractable needle, vacuum tube phlebotomy systems having retractable needles, and intravenous devices having retractable needles.

Once past the introductory portions of the patent, however, Jagger et al. confine their disclosure to hypodermic and phlebotomal uses. They never again mention any possibility of applying their invention to intravenous devices.

In other words, although the Jagger patent represents that it encompasses disclosures within the field of the present invention, that does not appear to be so. The Jagger disclosure fails to include any specific disclosure directed to safely inserting a cannula into a patient.

Jagger et al. do illustrate and describe a device that facilitates retraction of a hypodermic needle into a personnel-protective enclosure. They also show and describe another device that similarly facilitates retraction of a phlebotomy needle into a like enclosure. In both of these devices the retraction procedure is relatively cumbersome.

In the hypodermic device, the needle is mounted by a relatively tight press fit to the forward end of a syringe that is fitted within the handle. The needle also extends in a relatively loose press fit through a hole in the front of the handle.

After use, the syringe must be pulled bodily out of the back end of the handle, carrying the needle rearward out of its front-end press fit with the handle, and into the cavity within the handle. The needle is carried in a flange that is too wide to escape from the rear end of the handle, and accordingly is pulled away from its tight press fit to the front end of the syringe. It is thus trapped within the handle.

In the phlebotomy device, the blood-collection receptacle is initially enclosed within an outer housing/handle during use. The rear end of the needle passes in a tight friction fit through an elastomeric stopper on the receptacle.

Thereafter the receptacle is used as a tool to unscrew the needle from the forward end of the handle. Then the receptacle stopper is pulled off the rear end of the needle, so that the receptacle with its blood sample can be removed from the handle. As the receptacle is withdrawn, the needle is trapped by its flange in the handle.

Thus the two forms of the Jagger invention that are described require the user to actually pull the needle all the way back through the hole in the handle. This motion must be continued until the needle is entirely within the handle cavity.

It will be seen immediately that for a needle more than about an inch long this manipulation is difficult to accomplish using only one hand. The difficulty will be compounded if the maneuver must be performed with only part of the user's attention, as is often the case.

In most instances the necessary manual operations must include several motions in sequence. What is required is a compound motion, each stage of which is typically of relatively large amplitude in comparison with the length of the needle and the size of the user's hand.

As a matter of ergonomics, the requirement for such large-amplitude and compound motions is inherently adverse to definite, reliable and therefore safe retraction. This is particularly so for medical personnel under harried circumstances.

Other factors, specific to the hypodermic and phlebotomy applications of the Jagger invention, make the procedure even more awkward and difficult. First, as to the Jagger hypodermic needle, proper retraction depends upon maintenance of the design relationships between two friction levels. These relations are too easily upset.

For example, they can be disturbed by temperature variations in storage, beyond the knowledge of the person using the device. They can also be disturbed by leakage of congealable or sticky substances such as blood or sucrose solution, through the large opening at the rear of the handle and into the exposed seams between the handle and the needle flange.

The necessary friction relationships can also be disturbed by imperfect insertion of the syringe tip into its mating receptacle at the rear of the needle flange. That procedure, which in many cases is performed by medical technicians on site, rather than the manufacturer's personnel, can at least in principle damage either of the friction-fitting surfaces involved.

In such circumstances the syringe can be extracted from the needle flange before the needle is retracted—leaving no proper means for retraction.

As to the Jagger phlebotomy needle, the arrangement for retraction is even more adverse to reliable operation. The flange of the phlebotomy needle must actually be unscrewed before it can be pulled back into the handle.

In any event, it is not suggested how the Jagger invention might be configured or might function for use in a cannula insertion device. As previously mentioned, that is the field of the present invention.

Other prior patents describe devices for automatic or semiautomatic resheathing of hypodermic syringes. These, however, do not even mention the possibility of intravenous-cannula use.

U.S. Pat. No. 4,026,287 to Haller is among the better of these, since it at least provides for retraction of the used needle into a cavity in a unitary, sturdy structure. The Haller device, however, requires screwing the syringe plunger into the back of the needle flange after use, to destroy a frangible seal around the flange and then retract the needle.

Haller also fails to protect against inadvertent insertion of fingertips into the syringe barrel. Even more serious is the fact that Haller's syringe plunger can remain in place, held only by detents at the rear of the barrel.

The Haller plunger thus remains dangerously ready to drive the needle forward again if the syringe is accidentally jarred past the detents. In addition, Haller's device and most of the others discussed below are disadvantageous in that their after-use sheathing configurations are at least as long as—or in some cases longer than—the initial or before-use configurations.

A device to be discarded, particularly one that is dangerous if broken open, should not be so extended and should not have a multiple-stage structure. Such configurations invite breakage and potentially serious accident.

(It should be noted in passing that in the present context the title of Haller's patent may be somewhat misleading. That title is "Syringe with Retractable Cannula"—her term "cannula," however, does not refer to an indwelling-catheter cannula, but simply to the forward end of the syringe body.)

U.S. Pat. No. 4,631,057 to Mitchell also leaves the needle accessible to fingertips through the unsealed forward end of the sheath. Mitchell's device also shares with the Haller device an undesirable sensitivity to jarring the device out of its safety detents, and in addition a similar undesirable extended after-use configuration.

Other patented devices with a like vulnerability to jarring out of detents and a like extended postuse configuration, but at least providing better frontal shielding against fingertip insertion, are U.S. Pat. Nos. 4,573,976 (Sampson), 4,643,199 (Jennings, Jr. et al.) and 4,643,200 (Jennings, Jr.).

Worthy of mention for its provision of more positive resistance to jarring of the needle out of retracted position is U.S. Pat. No. 4,425,120 to Sampson et al. That device pays for its better safety locking with complexity of the manual manipulations required in use.

Similar observations apply to U.S. Pat. No. 3,890,971 to Leeson, which offers a relatively very compact and stable postuse configuration, but at the cost of a relatively complicated mechanism and large-amplitude motions to effect the resheathing.

Numerous devices for providing merely visual shielding or screening of hypodermic syringes have also been patented. Among these are U.S. Pat. Nos. 2,876,770 (White), 2,674,246 (Bower) and 3,134,380 (Armao). Such devices are actually counterproductive with respect to present purposes, since they effectively conceal the presence of a dangerously sharp and possibly contaminated needle.

Thus the prior art has failed to provide a suitable safety device for use under modern conditions in the field of the present invention—medical indwelling-cannula insertion. No prior-art device adequately protects people from contact with portions of the device that have been within the patient. In particular, no prior-art device provides the necessary sure and easy operation that is essential to the effectiveness of such protection.

SUMMARY OF THE DISCLOSURE

My invention is a safety device for use in inserting a cannula into a patient. It also serves thereafter to protect medical personnel, trash-handling personnel, and any other people who may have casual contact with the device after its use. The device protects all such individuals from contact with portions of the device that have been within the patient.

The device of my invention includes a needle for piercing the patient, and for guiding and carrying a cannula into place within the patient. The needle has a shaft with at least one sharp end.

My invention also has a hollow handle that is adapted to enclose at least the sharp end of the needle. The handle is particularly adapted to so enclose the sharp end beyond reach of such people's fingers.

In addition the invention includes some means for securing the shaft of the needle to the handle, with the sharp end projecting from the handle. For purposes of generality in description, I shall refer to these means as the "securing means."

My invention further includes some means for releasing the securing means—and for retracting the sharp end of the needle into the handle. These means I shall, again for generality, call the "releasing and retracting means." Retraction of the needle by these means is substantially permanent.

The releasing and retracting means of my invention are manually actuable by a simple unitary motion. By "simple unitary" motion I mean a motion that is not compound, one that entails a single-stage stroke or movement in just one direction.

The amplitude of this motion is substantially shorter than the length of the needle. Alternatively, it may be described as small compared with the size of the user's fingers, or hand generally.

The foregoing may be a description of my invention in its most general form. As will be appreciated, however, there are additional features which I prefer to incorporate in my invention to particularly optimize its efficacy.

Such desirable and preferred features include an aperture, defined in the handle, that is small compared with the fingers of such people to be protected—but large enough for passage of the needle. Another preferred feature is a trigger mechanism, forming part of the releasing and retracting means, that is operable from outside the handle.

The releasing and retracting means also preferably include some means—such as, for example, a coil spring—for positively biasing the sharp end of the needle toward retraction into the handle. After retraction has actually occurred, these biasing means preferably continue to operate, to retain the sharp end of the needle retracted within the handle.

My invention preferably includes a block that is fixed to and extending from the needle, and that forms a part of the securing means. The block is adapted to be restrained within the handle, with the sharp end of the needle projecting from the handle.

The block, when present, is also responsive to the releasing and retracting means, to withdraw the needle into the handle. The releasing and retracting means are preferably actuable by just one hand of a user of the device. It is also strongly preferable that a user can actuate these means without looking at the device during the actuation.

More specifically, I prefer to provide stop elements respectively defined within the handle and on the block. These elements engage each other to restrain the block from retracting the needle.

I also prefer to provide a trigger mechanism, including a manually operable release member. The trigger mechanism disengages the stop elements from one another to release the block and thereby retract the needle.

As previously mentioned, my device is for use with a cannula. The cannula fits over the needle and is guided by it into the patient's body.

Thus the cannula may be regarded as a part of the environment of my invention. For some purposes, however, to the extent indicated in the appended claims, it is appropriate to regard the cannula as a part of the invention itself.

All of the foregoing operational principles and advantages of the present invention will be more fully appreciated upon consideration of the following detailed description, with reference to the appended drawings, of which:

BRIEF DESCRIPTION OF THE DRAWINGS

FIG. 11 is a schematic enlarged side elevation, mostly in longitudinal section and drawn interrupted in two areas, of a conceptually generalized form of a certain group of embodiments of my invention, showing the needle in extended position for use in starting a cannula. It is to be very clearly understood that many other embodiments of my invention, some but not all of which are illustrated and discussed in this document, are outside the group of embodiments that is represented in generalized form by FIG. 11.

This same understanding applies equally to FIG. 12, which is a schematic perspective of the FIG. 11 generalized form of a certain group of embodiments.

FIG. 13 is a highly schematic enlarged perspective view of a fifth embodiment of my invention.

FIGS. 13a and 13b are like schematic side and end elevations, respectively, of the FIG. 13 embodiment.

DETAILED DESCRIPTION OF THE PREFERRED EMBODIMENTS

Figure 1:
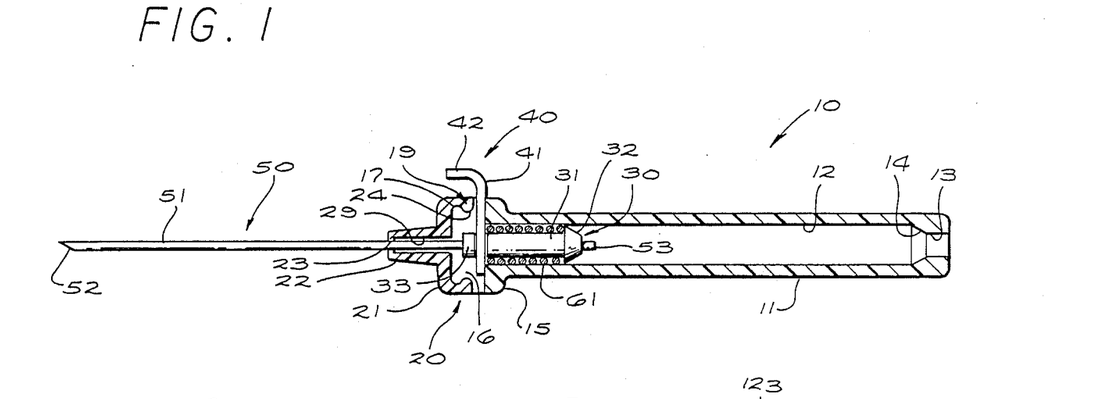
FIG. 1 is a side elevation, mostly in longitudinal section, of a preferred embodiment of my invention, shown with the needle secured in extended position for starting a cannula.
Figures 2, 3, 3A:
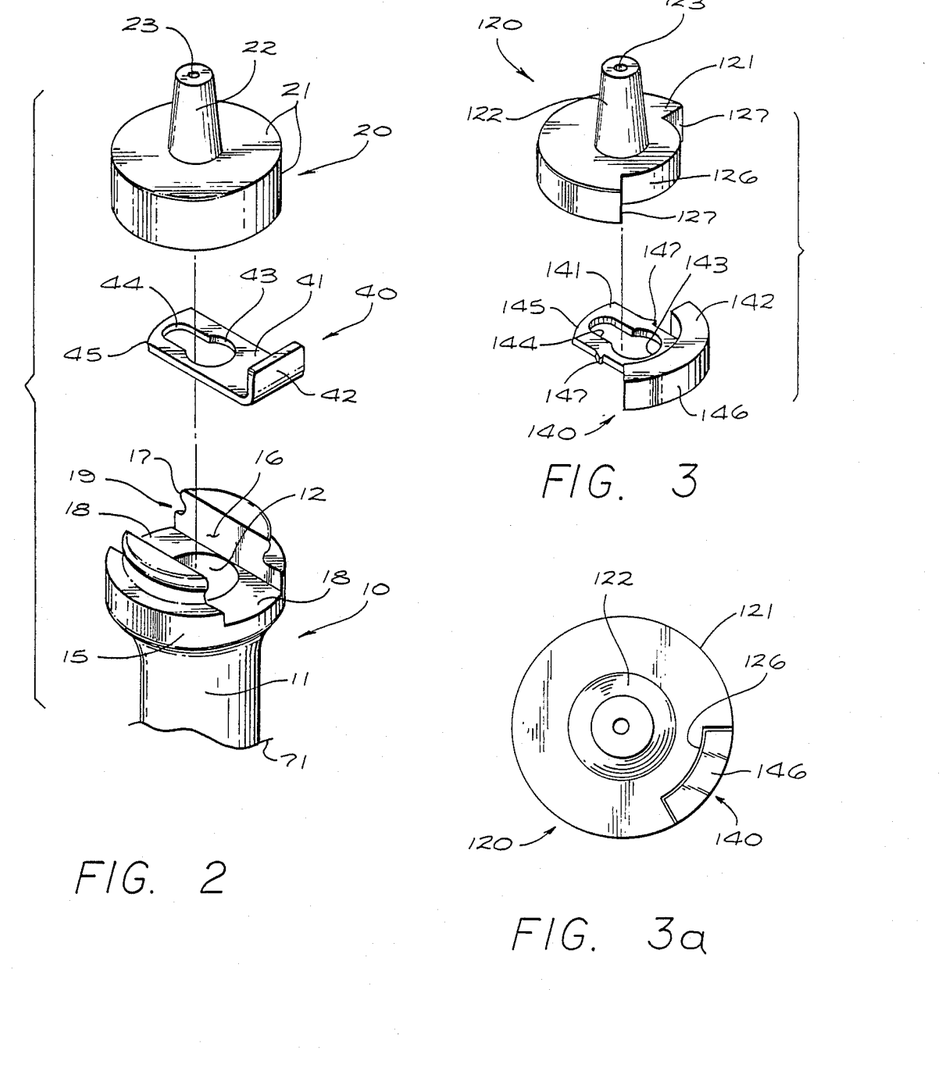
FIG. 2 is an enlarged and exploded perspective drawing, drawn interrupted at one end, of some of the parts of the FIG. 1 embodiment.
FIG. 3 is a similar view of a variant form of some of the FIG. 2 parts.
FIG. 3a is a somewhat schematic end elevation of the FIG. 3 parts assembled.

As shown in FIGS. 1 and 2, an embodiment of my invention which I now prefer includes a shaped hollow handle 10. This embodiment also includes a nosepiece 20 that is securely fixed to a forward end of the handle 10, and a carrier block 30 that is slidably disposed within the handle 10.

The embodiment of FIGS. 1 and 2 also includes a latch 40 that secures the carrier block 30 near the forward end of the handle, close to the nosepiece 20; and a needle 50 that is carried by the block 30 and extends from the handle 10 through the nosepiece 20. Finally, this embodiment includes a spring 60 that is positioned within the handle 10 and encircles part of the carrier block.

The various parts of this embodiment of my invention are particularly configured for ease and economy in manufacture. Accordingly in the description of this embodiment I shall mention many details of configuration. I mean it to be understood that all such details are included to enable a person skilled in the art to practice my invention in its best mode as currently envisioned, and in particular very cost-effectively.

The handle 10 is preferably but not necessarily injection molded from plastic such as polycarbonate. It includes a long, generally right-circularly cylindrical outer grip surface 11, radially enlarged near its forward end to form a thumb stop 15.

The thumb stop, in turn, is the rearward part of a latch-housing portion 15-19—better seen in FIG. 2. The thumb stop 15 is a right-circular cylinder, much shorter than but conaxial with the outer grip surface 11.

The remainder of the latch-housing portion 15-19 is also circularly symmetrical, except that it is bisected at its forward end by a broad transverse latch-guide slot 16, 18. The transverse latch-guide slot 16, 18 has a bottom surface 18 and two opposed side walls 16.

As viewed from the end of the device, each side wall 16 of the latch-guide slot 16, 18 is formed along a chord of the circular shape of the thumb stop 15. Thus in effect the latch-guide slot 16, 18 divides the forward portion of the latch housing 15-19 into two identical upstanding pillars as seen clearly in FIG. 2. Each pillar is formed as a segment on the chord.

A circumferential groove 19, also better seen in FIG. 2, is formed near the forward end of the latch housing 15-19. This groove 19 is spaced away from the bottom surface 18 of the latch-guide slot 16, 18. At the very end of the latch housing there is a flange 17, of diameter smaller than that of the thumb stop 15.

I prefer to form neither the groove 19 nor the flange 17 as rectangular in longitudinal section. Rather, to facilitate removal from an injection mold—and also to ease snap-together assembly with the nosepiece 20—I prefer to form the groove 19 and the flange 17 as arcs in longitudinal section.

A centered longitudinal bore 12 is formed within the handle 10, exposed at the bottom surface 18 of the latch-guide slot 16, 18. This bore is very generally right-circularly cylindrical, but preferably has a very slight taper or draft widening toward the rear end of the handle to facilitate removal of the handle from a mold.

Near the rear end of the bore 12, however, there is formed an internally frustoconical stop surface 14—narrowing the bore 12 slightly. At the extreme end of the bore 12 is a short end section 13, opening at the rear end of the handle 10.

The end section 13 of the bore is preferably slightly tapered outward toward the rear, and (notwithstanding the drawing) of the same length and taper as the needle guide 22. The taper of the frustoconical stop surface 14 is slight, and the overall diametral inset from the long section 12 of the bore to the end section 13 of the bore is very slight.

By virtue of these details of configuration, the handle can be popped out of an injection or other mold by means of a slight deformation (expansion) of the rear end. That is, a separate core piece in the mold is not needed.

The nosepiece 20 is a right-circularly symmetrical article with two main sections: a relatively slender forward needle guide 22 and a radially enlarged rearward canopy 21. The needle guide 22 has a central bore that is somewhat larger than the diameter of the needle 50.

At the extreme tip of the needle guide 22 this central bore narrows to a fine aperture 23. The diameter of the end aperture 23 is chosen as a tradeoff between (1)

complete stabilization of the needle and (2) minimum friction in sliding clearance between the guide 22 and needle.

The canopy 21 has a right-circularly cylindrical outer surface, preferably matching the outer surface of the thumb stop 15. Formed in the rear end of the canopy is a cavity, internally shaped to mate securely with the contours of the latch housing 15-19.

More particularly, at the very end of the cavity there is an inward flange or lip 24 (FIG. 1) that accurately fits into and engages the groove 19 of the latch housing 15-19. Due to the previously mentioned spacing of the groove 19 away from the bottom surface 18 of the latch-guide slot 16, 18, the inward lip 24 of the nosepiece 20 is similarly spaced from the bottom surface 18. The resulting gap defines a track for operation of the latch 40.

The nosepiece can be made of the plastic available commercially under the trade name "Delrin." That material is selected primarily because it is easy to form.

The carrier block 30 has a very narrow central bore in which the needle 50 is tightly gripped. The block 30, also of Delrin, may be press-fit, shrink-fit, and/or cemented on the needle, or molded in place.

The outside of the carrier block 30 is circularly symmetrical. It has an extended barrel 31 that may be right-circularly cylindrical. At the rear end of the barrel 31 is a frustoconical stop section 32 whose forward end is radially enlarged relative to the barrel 31. The stop section tapers inward toward the extreme rear of the block 30.

The rear, frustoconical surface of the stop section 32 is shaped to seat against the previously mentioned internal frustoconical stop section 13 of the handle 10, when the needle is fully retracted. The front end of the stop section 32 forms a generally planar, annular, step radially outward from the barrel 31, for purposes to be seen shortly.

The forward end section 33 of the block 30 is of the same diameter as the barrel section 31. Between the forward end section 33 and the barrel 31, however, there is formed a circumferential latch groove. Thus the forward end section 33 forms a flange adjacent to and just forward from the latch groove.

The latch 40 has a flat slide section 41, and at one end of the slide a short pushbutton section 42 bent or formed at right angles to the slide 41. A keyhole-shaped cutout 43, 44, is defined in the slide.

The enlarged portion 43 of this cutout is nearer to the pushbutton 42. The end 45 of the slide 41 opposite the pushbutton 42 lies immediately past the narrowed portion 44 of the cutout 43, 44. The latch can be made from a suitably selected 300 series stainless steel.

The needle 50, with its shaft 51, sharpened tip 52, and rear end 53, is generally conventional—and also of stainless steel. It is longer than usual, to allow for the extra length required to pass into and through the carrier block 30. The block 30 is fixed upon the needle shaft 51 very near the rear end 53 of the needle.

Finally the preferred embodiment of FIGS. 1 and 2 includes a coil spring 61, sized to encircle the outside diameter of the carrier-block barrel 31. The spring should be long enough to hold the mechanism fully retracted. The minimum diameter of the handle bore 12 is selected to just enclose the spring 61—without significantly restricting the free expansion of the spring.

To assemble the device, the carrier block 30 is first fixed to the needle 50 as previously described. Then the needle 50 is inserted through the spring 61, until the carrier block 30 reaches the spring. This same general motion is then continued, to insert the flange 33 and barrel 31 of the carrier block through the spring 61.

The result of this procedure is that one end of the spring is seated against the previously mentioned step at the rear end of the carrier-block barrel 31.

Next the needle is inserted into the keyhole cutout 43, 44 in the slide 41, until the carrier block 30 reaches the slide 41. The same general motion is continued, passing the flange 33 at the forward end of the carrier block through the enlarged section 43 of the keyhole cutout 43, 44 in the slide 41.

The result of this procedure is to align the slide 41 longitudinally with the circumferential groove (between the barrel 31 and flange 33) in the carrier block 30. Next the slide 41 is moved laterally toward the pushbutton 42 so that the narrower portion 44 of the keyhole cutout 43, 44 is captured in the circumferential groove in the block 30.

The carrier block 30, with the needle 50, spring 60 and latch 40 in effect threaded upon it as just described, is then inserted rear-end-first into the front end of the bore 12 in the handle 10.

The slide 41 thus fits between the two side walls 16 of the latch-guide slot 16, 18, and rests against the bottom surface 18 of the slot. The needle is then inserted through the bore 29 and clearance aperture 23 in the nosepiece 20; and the shaped forward end 16, 17, 19 of the latch guide is then snapped in place within the canopy 21 of the nosepiece 20.

The handle 10 is now in effect longer, by the added length of the nosepiece 20. When assembled in this way, the slide portion 41 of the latch 40 is positioned in the previously mentioned "track" that is defined between the bottom surface 18 (FIG. 2) of the latch-guide slot 16, 18 and the inner lip 19 (FIG. 1) of the nosepiece 22.

The pushbutton 42 is pulled fully outward radially from the latch-guide housing 15-19 (or, to now put it more completely, 15-21). The needle 50 is now firmly secured in position, extending forward from the effectively lengthened handle.

After the nosepiece 20 is snapped into place on the end of the handle 10, these two parts are preferably secured together as by sonic welding. (If preferred they can be held together by cement, naturally applied before assembly, or by through pins, etc.) This procedure is desirable to ensure permanence of attachment—and thus permanence of capture of the needle after retraction.

My invention makes use of a cannula generally similar to the conventional one shown in FIG. 16. Since, as can be seen, the safety insertion set of my invention is slightly longer than some prior-art insertion sets, I prefer to shorten the cannula hub slightly to minimize the overall length of my invention.

Depending upon the precise shaping of the forward portions of my invention, cannulae for use with my invention thus may be entirely conventional, or advantageously may be adapted by shortening of the hub.

For simplicity and clarity of the drawings of my invention, I have omitted the cannula from them. All of FIGS. 1 through 15, however, are to be taken as incorporating the cannula in its positioning over the needle shank, by reference to FIG. 16.

The rearmost bore 13 of the handle 10 should preferably be given the same diameter as the internal diameter of the cannula hub. It should also be given the same overall length, though FIG. 1 does not so illustrate it. Thus the prior-art feature of temporary fluid connectability through the hollow needle 50 can be preserved in my apparatus.

In addition, a very generally conventional safety cover for the needle of my invention should also be provided, to protect against accidental puncture and against contamination of the needle before use. The cover must be adapted to fit over the pushbutton 42 without triggering it—and preferably also to fit between the pushbutton 42 and the canopy 21, to deter movement of the slide 41 due to vibration in shipment or other handling.

After use, however, the safety cover may be thrown away. In particular, it may be discarded either together with my invention or separately, since the needle is automatically sheathed without that cover.

Dimensions of the nosepiece needle guide 22 and rear bore 13 of my preferred embodiment should be the same as the dimensions of standard cannulae, to mate with standard tubing. Both should be roughly 0.275 inch long, and taper from 0.15 inch at the front to 0.20 inch at the rear.

Other dimensions of my preferred embodiment of FIG. 1 are roughly (in inches):
3.5: length from rear end of handle to forward surface of canopy
2.3: length from forward surface of canopy to tip of needle
0.500: outside diameter of nosepiece canopy
0.350: outside diameter of handle grip surface
0.165: inside diameter of handle bore near trigger
0.170: inside diameter of handle bore near rear end
0.625: length of carrier block
0.165: outside diameter of carrier-block stop section
0.120 outside diameter of carrier-block barrel.

Although I consider the embodiment described above highly desirable, various features could in principle be omitted and the device still correspond to my invention as most broadly envisioned. For example, a tension spring (rather than a compression spring as shown) could be secured to a small hole or hook near the rear end of the needle, to pull the needle into a closed handle without the intermediary of a carrier block.

Alternatively the spring could be omitted, and the needle arranged to fall into the handle under the influence of gravity when a latch is released. Furthermore, it is not strictly necessary that the needle be hollow: that is only important if it is desired to maintain the user's option to make temporary fluid connection through the needle.

Moreover it is not necessary that the rear end of the needle initially be within the handle. Some other element of the apparatus could instead pull the rear end of the needle into the handle when a latch is released.

On the other hand, it is not necessary that after actuation of the latch the rear end of the needle come to rest within the handle: in principle the "back" of the needle could protrude from the rear end of the handle. In this case proper provision must be made, however, to prevent the needle from being accidentally reextended forward through the nosepiece.

Most or all of these variations, as will be seen, are applicable to other embodiments of my invention that are shown in FIGS. 3 through 15 and discussed below. For positive, maximally safe operation, I personally prefer not to employ any of the variations described in the preceding four paragraphs. Nevertheless some or all of them could possibly or probably be made safe and convenient by careful design, and they are accordingly within the scope of certain of my appended claims.

I have had a working model of the FIGS. 1 and 2 embodiment constructed, and I have found its operation excellent. That embodiment, however, may be subject to improvement.

For example, I believe that the variant that is illustrated in FIGS. 3 and 3a may be preferable, though I have not constructed a working model for direct comparison. In FIGS. 3 and 3a the pushbutton is a formed annular-segment plastic piece 142, with an antislip peripheral surface 146; and the nosepiece has a section 126, 127 cut out to accommodate the pushbutton 146.

This configuration seems probably preferable, for ease of operation. The fingers of a person using the device will normally be kept behind the thumb stop 15 (FIGS. 1 and 2), and therefore are unlikely to accidentally operate the button 146.

Even in event of such an accident, there is no harm to the patient or medical personnel. The main adverse result is economic: another insertion set must be obtained. Regular users of the device will quickly learn to avoid inadvertent triggering of the latch.

Another refinement shown in FIG. 3 is that ratchet-shaped detents 147 are provided on the edges of the slide, to interact with corresponding features (not illustrated) formed in the side walls 16 of the guide slot 16, 18. These detents 147 will prevent the trigger from being reset, and thereby discourage attempts to reuse the needle.

I shall now mention still another desirable characteristic of my preferred embodiment, perhaps not clearly illustrated. I prefer to slightly increase the diameter of the large end of the frustoconical stop section 32 of the carrier block, so that it provides a fluid seal against the inside bore 12 of the handle 10—when the trigger is not actuated.

This arrangement facilitates effective fluid communication through the hollow needle by minimizing reliance on maintenance of sanitation at the many intricate surfaces of the spring, internal cavities, etc., that are forward of the stop section 32.

Various features or elements appear in FIGS. 3 and 3a that have not been specifically identified above. Those features or elements are substantially identical to the items in FIGS. 1 and 2 that have corresponding reference numerals—i.e., numerals that differ only by addition of the prefix "1" in FIGS. 3 and 3a.

Figure 4:
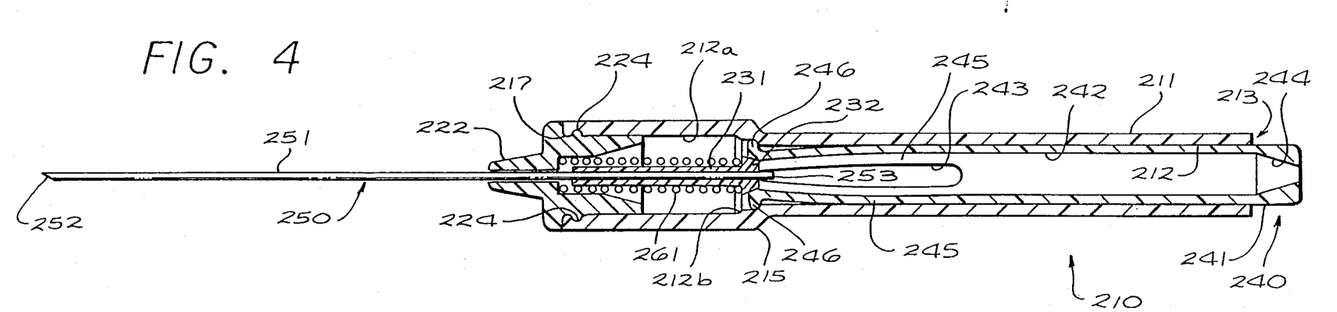
FIG. 4 is a side elevation, mostly in longitudinal section, of a second embodiment of my invention, showing the needle in extended position for use in starting a cannula.
Figure 5:
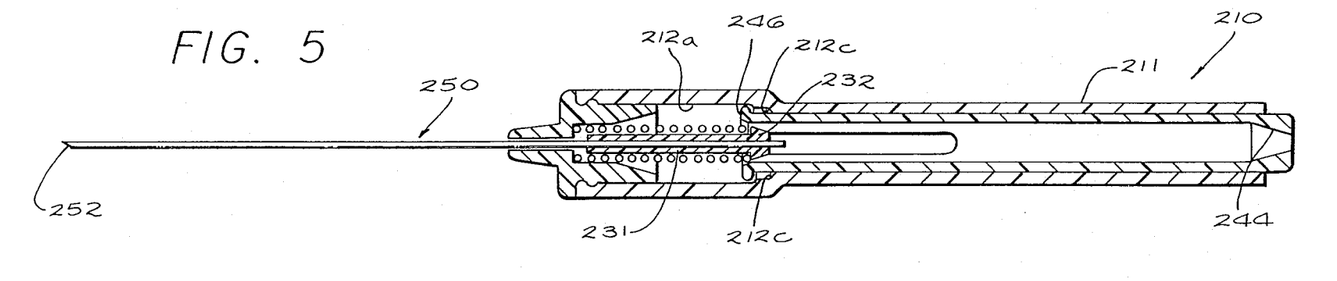
FIG. 5 is a similar view of the FIG. 4 embodiment, showing the device a fraction of a second after the release mechanism is actuated, with the needle moved very slightly back from its FIG. 4 position toward its retracted position.
Figure 6:
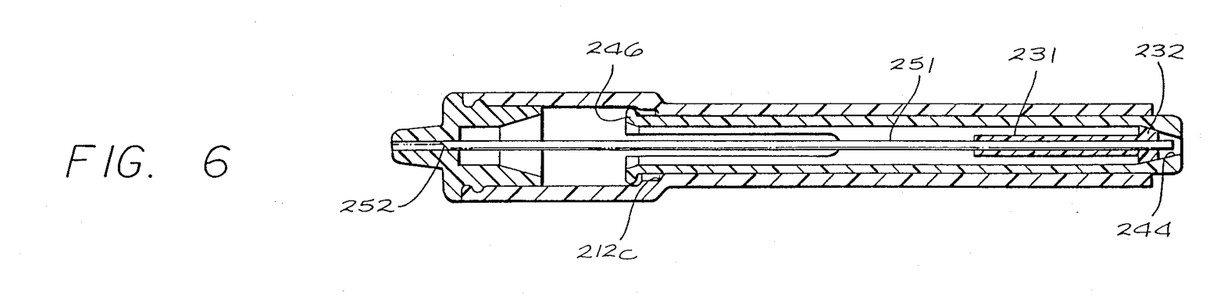
FIG. 6 is a similar view of the FIG. 4 embodiment, showing the needle fully retracted.

FIGS. 4 through 6 illustrate another embodiment of my invention. Here the corresponding parts have reference numerals varying by addition of the prefix "2".

In the embodiment of FIGS. 4 through 6, the latch is triggered by pressing the rear end of the handle against any surface: a tabletop, the user's arm, or even part of the patient's arm. This form of my invention may be preferable in environments where a tabletop or other suitable positive-actuating surface is available.

It may be found unsatisfactory, however, where only softer surfaces such as bedding or the patient's body can be used. Another aspect of this embodiment that may be found undesirable is a slightly greater outside diameter of the grip surface 211.

The carrier block 231–232 of FIGS. 4 through 6 is generally like that in FIG. 1. Here, however, the spring 261 seats directly against the inside surface of the nosepiece 222.

A latch cylinder 241 is inserted through the rear of the handle 210 into a bore 212. Roughly the front third or half of the latch cylinder 241 is split into two (or more) flexible fingers 245, which terminate at their forward ends in lips or flanges 246 that point radially outward.

The bore 212 inside the handle 210 is enlarged, proceeding toward the front of the device, in two definite steps. The first step, outward to the bore 212c (FIGS. 5 and 6), provides a ledge for capture of the lips or flanges 246 to deter the latch cylinder 241 from falling rearward out of the handle 211.

When the fingers are in position against the bore 212c, the carrier-block frustoconical stop section 232 is pressed by the spring 261 against pretrigger stop surfaces formed by the insides of the ends of the fingers 245. This is the pretrigger condition shown in FIG. 4.

The second step, outward to the bore 212a, provides radial escape room for expansion of the fingers away from the carrier-block stop section 232. Thus when the rear end of the latch cylinder 241 is pressed forwardly from its FIG. 4 position, it at first drives the carrier block and needle very slightly forward until the lips 246 reach the second step. The lips 246 then spring outward against the bore 212a, to their positions shown in FIG. 5.

The carrier-block stop section 232 is no longer obstructed by the pretrigger stop surfaces formed by the ends of the fingers 245. The block 231, 232 with the needle 250 is accordingly propelled rearward by the coil spring 261.

FIG. 5 shows the block 231, 232 and needle 250 an instant after the beginning of this motion. As illustrated they are just started rearward into the bore 242 of the latch cylinder 241.

Eventually the carrier-block stop section 232 engages the inner stop surface 244 at the rear of the latch cylinder 241, as shown in FIG. 6. The needle is then retained fully retracted within the handle 210 and latch cylinder 240.

Figures 7, 8:
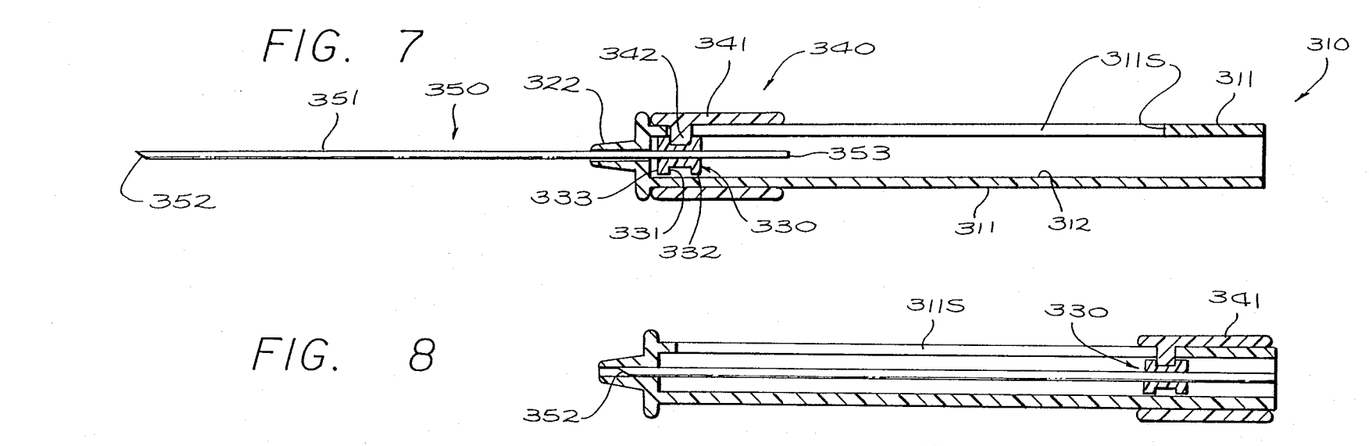
FIG. 7 is a similar view of a third embodiment of my invention, showing the needle in extended position for use in starting a cannula.
FIG. 8 is a similar view of the FIG. 7 embodiment, showing the needle fully retracted.

The embodiment of FIGS. 7 and 8 may be useful where a solid (that is, not hollow) needle 350 can be employed. Such needles, as previously mentioned, are acceptable if it is not necessary to allow for the desirability of pretriggering temporary fluid connection through the needle.

Some cost saving is effected by using a needle that is solid, and this saving can be further enhanced by using a mechanism that need not be fluid-tight and sanitary inside. One such mechanism is shown in FIGS. 7 and 8.

Here the needle carrier block is a simple spool—a short necked-down barrel 331 separating two flanges 332, 333. To put it another way, a circumferential groove 331 is formed partway along the carrier-block barrel 331, 332.

A needle-retraction sleeve 340 slides on the outside of the cylinder 311. A retraction-actuator pin 342 extends inwardly from the retraction sleeve 340, through a slot 311s in the wall 311, 312 of the handle 310, and into the groove 331 in the carrier block 330.

Before and during insertion of a cannula with the FIGS. 7 and 8 embodiment, firm detents (not shown) hold the block 330, needle 350 and sleeve 340 at the front of the handle 310. This condition, illustrated in FIG. 7, continues until the cannula is in place within the patient's body.

Then the user of the device holds the rear end of the handle 310 firmly against a solid surface, and manually pulls the retraction sleeve 340 rearward out of the detents. As the user moves the retraction sleeve, its retraction pin 342 forces the carrier block 330 and needle to move correspondingly rearward.

When the sleeve 340 is operated fully to the rear of the handle 310, positive-acting ratchet-type detents come into play to prevent the sleeve from being advanced. These detents thus lock the needle in its retracted position.

Figures 9, 10:
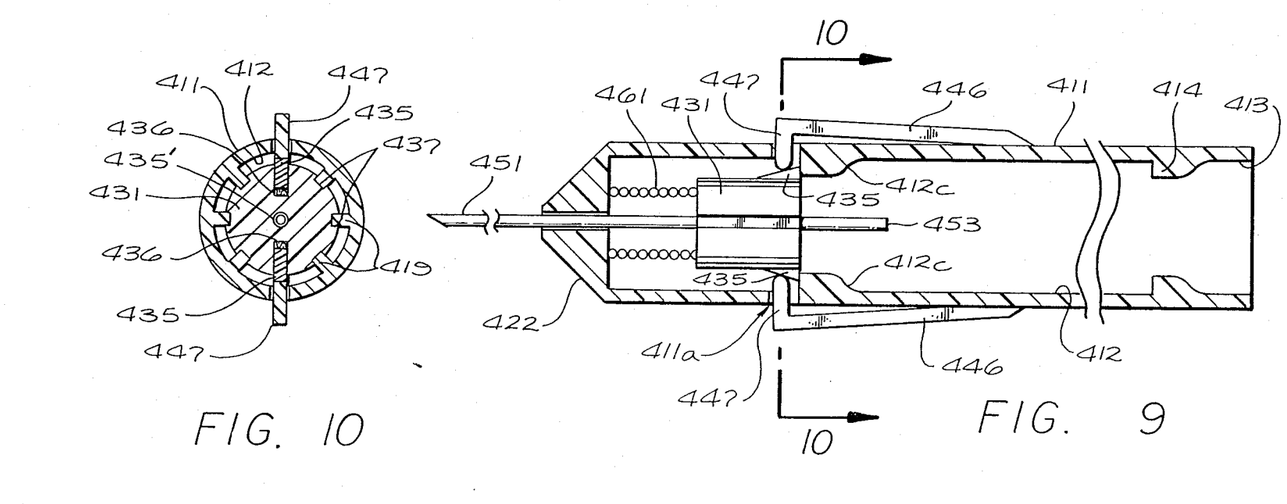
FIG. 9 is a somewhat schematic enlarged side elevation, mostly in longitudinal section and drawn interrupted in two areas, of a fourth embodiment of my invention.
FIG. 10 is a somewhat schematic enlarged elevational cross-section of the same embodiment, taken along the line 10—10 in FIG. 9.

Yet another embodiment appears in FIGS. 9 and 10. Whereas the movable latch elements of FIGS. 1 through 6 are mounted to the respective handles of the illustrated devices, and there is no latch as such in FIGS. 7 and 8, the movable latch elements of FIGS. 9 and 10 are mounted to the carrier block.

More particularly, radially extending latch ears 435 (FIG. 10) are restrained within guide holes in the outside of the carrier block, but biased radially outward by springs 436. These latch ears 435 engage thickened portions 412c of the handle wall 411, 412, preventing rearward motion of the carrier block 431 and needle.

After use, the user squeezes latch-actuator fingers 446, at opposite sides of the handle exterior 411. The tips of these fingers are formed with small inwardly extending bosses 447.

When the user squeezes the fingers 446 inward, the bosses 447 force the latch ears 435 inward against the action of the springs 436, disengaging the ears from the thickened wall portions 412c. A coil spring 461 then propels the carrier block and needle rearward as in the embodiments of FIGS. 1 through 6.

After passing the thickened wall portions 412c, the latch ears are again biased radially outward from the carrier block. Accordingly, when the block reaches the rear end of the handle and the needle is fully sheathed, the latch ears engage the rear stops 414 to halt the retraction.

Figures 11, 12, 13, 13A, 13B:
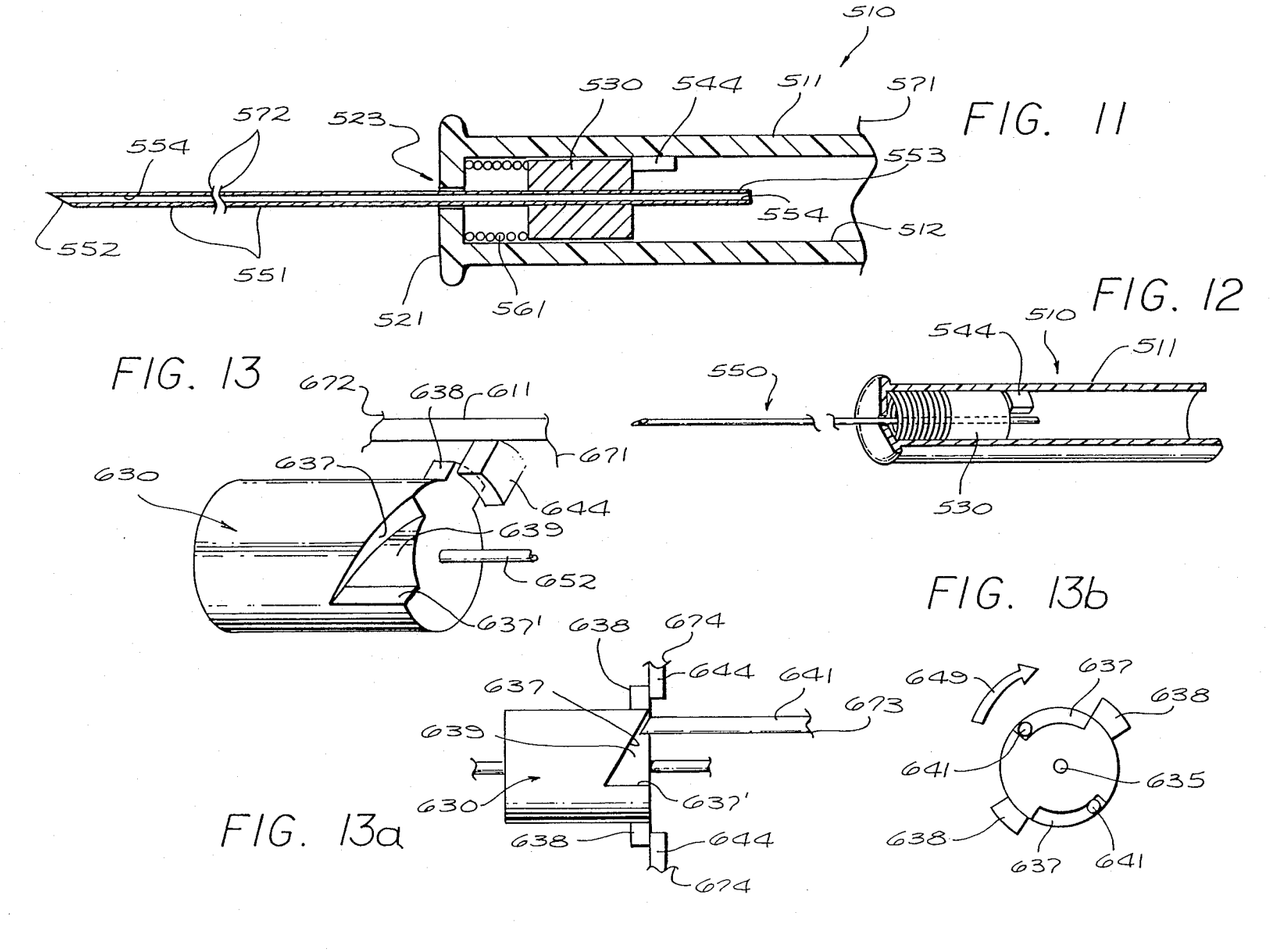

FIGS. 11 and 12 are included to indicate in a schematic way that carrier-block-and-spring embodiments of my invention may generally include any mechanical arrangement of the general character shown. In these drawings, a releasable latch element 544 temporarily secures a carrier block 530 at the forward end of a handle-cylinder 511.

In the general arrangement shown, the sharp end 552 of a needle projects through a forward aperture 523 and out of the forward end 521 of the handle. A spring 561 biases the carrier block 530 rearward.

Any such configuration (as well as others not encompassed within the general relationships illustrated) is currently believed to be within the scope of my invention. It is immaterial whether movable latch elements are mounted to the carrier block 530, the handle 510, or both.

Generally speaking, the overall length of any such device will be the sum of two distances. The first of these is twice the length of the narrow part of the cannula—a distance that is essentially fixed by the needed length of the cannula.

The second distance is the distance from the front of the nosepiece to the rear of the needle. The distance from the front of the nosepiece to the rear of the needle equals the sum of the lengths of the cannula hub, the fully compressed spring, and the rear stop surface of the carrier block.

These lengths, generally speaking, are controllable to some degree through careful design. They should be minimized.

FIGS. 13, 13a and 13b show a configuration in which two latch elements 638, 644 are respectively mounted to the carrier block 630 and handle wall 611. Neither element 638 or 644 moves radially or longitudinally.

An actuator mechanism is present, however, that provides relative rotation of the block 630 and handle. When this mechanism is operated, it offsets the two elements 638, 644 and releases the carrier block 630 for retraction.

The actuator mechanism includes a pair of helical surfaces 637 that are cut into opposite sides of the rear periphery of the carrier block 630. Necessary relief for these structures is provided by planar end walls 638 and cylindrical inside walls 639 as illustrated.

The actuator mechanism also includes a pair of actuator pins 641 that are forced through apertures in an end wall (not shown) of the handle, and against the helical surfaces. When the user operates the actuator pins 641, the block rotates within the handle as suggested by the arrow 649 in FIG. 13b.

Figure 14:
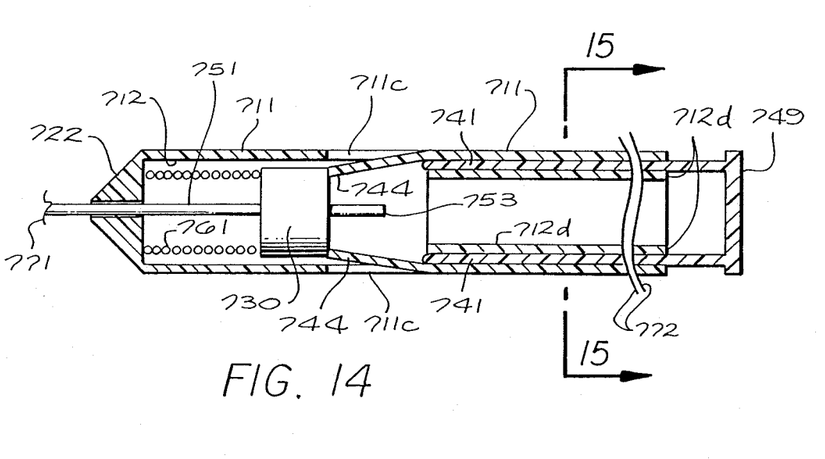
FIG. 14 is a somewhat schematic enlarged side elevation, mostly in longitudinal section and drawn interrupted in two areas, of a fifth embodiment of my invention—with the needle in extended position for use in starting a cannula.
Figure 15:
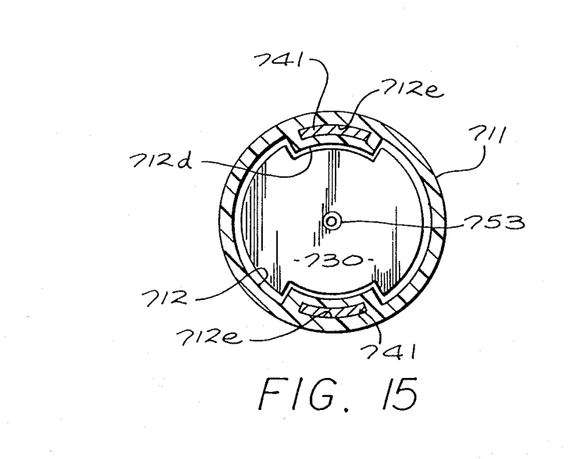
FIG. 15 is a somewhat schematic enlarged elevation of the same embodiment in cross-section, taken along the line 15—15 in FIG. 14—but with the needle retracted.

One other embodiment of my invention is shown in FIGS. 14 and 15. Here the movable latch elements are flexible fingers 744 formed as cutouts from portions of the handle wall 711 itself. These latch fingers 744 engage the rear side of the carrier block 730, restraining it against action of the coil spring 761.

To release the block 730 for retraction, the user pushes forwardly on an actuator button 749 at the rear of the handle. This may alternatively be accomplished, as described with regard to FIGS. 4 through 6, by pushing the handle rearward against a reaction surface.

Here the button 749 slides actuator pins 741 forward, relative to the handle, within guideways 712d, 712e. The actuator pins force the latch fingers 744 radially outward, releasing the block 730. As noted in the description of figures, these drawings are merely schematic.

It will be understood that the foregoing disclosure is intended to be merely exemplary, and not to limit the scope of the invention—which is to be determined by reference to the appended claims.

I claim:

1. A safety device for use in inserting a cannula into a patient and for thereafter protecting people from contact with portions of the device that have been within the patient; said device comprising:
   a needle for piercing such patient and for guiding and carrying such a cannula into place within such patient, said needle having a shaft with at least one sharp end;
   a hollow handle adapted to enclose at least the sharp end of the needle beyond reach of such people's fingers;
   means for securing the shaft to the handle, with the sharp end projecting from the handle; and
   means for releasing the securing means and for substantially permanently retracting the sharp end of the needle into the handle and beyond reach of such people's fingers;
   said releasing and retracting means being manually actuable by a simple unitary motion, of amplitude that is substantially shorter than the shaft of the needle.

2. The safety device of claim 1, wherein:
   the handle defines an aperture that is small compared with such people's fingers but large enough for passage of the needle.

3. The safety device of claim 1, wherein the releasing and retracting means comprise:
   a trigger mechanism operable from outside the handle.

4. The safety device of claim 1, wherein the releasing and retracting means comprise:
   means for positively biasing the sharp end of the needle toward retraction into the handle.

5. The safety device of claim 4, wherein:
   the biasing means also operate to retain the sharp end of the needle retracted within the handle.

6. The safety device of claim 1, wherein the securing means comprise:
   a block fixed to and extending from the needle, and adapted to be restrained within the handle with the sharp end of the needle projecting from the handle; and adapted for motion within the handle, responsive to the releasing and retracting means, to withdraw the needle into the handle.

7. The safety device of claim 1, for use with such a cannula that has a standard-size rear tubing fitting, for passage of liquids between the patient's body and equipment outside the patient's body after the needle is removed from the patient; and wherein:
   the needle is hollow, for passage of such liquids while the needle is within such patient; and
   the hollow handle has a standard-size rear fitting for attachment of such tubing while the needle is within the patient;
   whereby such liquids pass between the tubing and the patient by way of the needle and the handle rear fitting temporarily, while the needle is within the patient.

8. The safety device of claim 1, wherein:
   the releasing and retracting means are actuable by one hand of a user of the device.

9. The safety device of claim 1, wherein:
   the releasing and retracting means are manually actuable by a user of the device, employing just one hand and without looking at the device.

10. The safety device of claim 1, in further combination with:
    such cannula.

11. A safety device for use in inserting an intravenous cannula into a patient's blood vessel and for thereafter protecting people from contact with portions of the device that have been within the patient; said device comprising:
    a hollow needle for piercing such patient and for guiding and carrying such a cannula into place within such patient's blood vessel, said needle having a hollow shaft with at least one sharp end;
    a hollow handle that defines an aperture which is small compared with such people's fingers but large enough for passage of the needle, and that is otherwise adapted to enclose at least the sharp end of the needle;
    a block fixed to and extending from the needle, and restrained within the handle with the sharp end of the needle projecting out of the handle through the aperture, and adapted for motion within the handle to withdraw the needle into the handle; and
    a trigger mechanism, actuable from outside the handle for releasing the block, and including positive biasing means for forcibly moving the block within the handle to substantially permanently retract the sharp end of the needle into the handle and beyond reach of such people's fingers.

12. The safety device of claim 11, wherein:
the trigger mechanism is actuable by one hand of a user of the device.

13. The safety device of claim 11, wherein:
the trigger mechanism includes a projection from the handle, adapted for manual actuation by a user of the device to release the block.

14. The safety device of claim 11, wherein:
a guideway is defined within the handle to guide the block rearward from the aperture.

15. The safety device of claim 11, wherein:
a stop is defined within the handle, opposite the aperture, for halting the motion of the block after actuation of the trigger mechanism;
whereby the block and needle are retained within the handle.

16. The safety device of claim 11, for use with such a cannula that has a standard-size rear tubing fitting, for passage of liquids between the patient's body and equipment outside the patient's body after the needle is removed from the patient; and wherein:
the needle is hollow, for passage of such liquids while the needle is within such patient; and
the hollow handle has a standard-size rear fitting for attachment of such tubing while the needle is within the patient;
whereby such liquids pass between the tubing and the patient by way of the needle and the handle rear fitting temporarily, while the needle is within the patient.

17. The safety device of claim 11, in further combination with:
such cannula.

18. The safety device of claim 11, further comprising:
a stop element extending laterally from the block;
means for biasing the stop element outward from the block; and
a stop surface, defined within the handle, that engages the stop element to restrain the block from moving within the handle; and
wherein the handle has an external surface; and
the trigger mechanism includes a manually operable release member, accessible at or through the external surface of the handle, for forcing the laterally extending stop element inward against the action of the outward biasing means to release the block.

19. The safety device of claim 11, further comprising:
a stop element extending laterally within the handle;
means for biasing the laterally extending stop element inward from the handle; and
a stop surface, defined on the block, that engages the laterally extending stop element to restrain the block from moving within the handle; and
wherein the handle has an external surface; and
the trigger mechanism includes a manually operable release member, accessible at or through the external surface of the handle, for forcing the laterally extending stop element outward against the action of the inward biasing means to release the block.

20. The safety device of claim 11, further comprising:
stop elements respectively defined within the handle and on the block, for engaging each other over a limited range of angular positions of the block within the handle to restrain the block from retracting the needle; and
wherein the handle has an external surface; and
wherein the trigger mechanism includes a manually operable release member, accessible at or through the external surface of the handle, for forcibly rotating the block out of said range of angular positions to release the block.

* * * * *